United States Patent
Aschbacher et al.

(10) Patent No.: US 10,785,581 B2
(45) Date of Patent: Sep. 22, 2020

(54) RECURSIVE NOISE POWER ESTIMATION WITH NOISE MODEL ADAPTATION

(71) Applicant: MED-EL Elektromedizinische Geraete GmbH, Innsbruck (AT)

(72) Inventors: Ernst Aschbacher, Innsbruck (AT); FLorian Frühauf, Rinn (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 16/302,711

(22) PCT Filed: Jun. 12, 2017

(86) PCT No.: PCT/US2017/036968
§ 371 (c)(1),
(2) Date: Nov. 19, 2018

(87) PCT Pub. No.: WO2017/218386
PCT Pub. Date: Dec. 21, 2017

(65) Prior Publication Data
US 2019/0124454 A1 Apr. 25, 2019

Related U.S. Application Data

(60) Provisional application No. 62/349,175, filed on Jun. 13, 2016.

(51) Int. Cl.
*H04R 25/00* (2006.01)
*G10L 15/20* (2006.01)
(Continued)

(52) U.S. Cl.
CPC ....... *H04R 25/505* (2013.01); *A61N 1/36039* (2017.08); *G10L 15/20* (2013.01);
(Continued)

(58) Field of Classification Search
CPC .............. H04R 25/505; H04R 2225/43; H04R 2225/67; A61N 1/36039
(Continued)

(56) References Cited

U.S. PATENT DOCUMENTS

| 5,012,519 A | 4/1991 | Adlersberg et al. |
| 2007/0055508 A1 | 3/2007 | Zhao et al. |

(Continued)

FOREIGN PATENT DOCUMENTS

| DE | 10 2011 004338 B3 | 7/2012 |
| EP | 2916320 A1 | 9/2015 |
| WO | WO 2017/218386 A1 | 12/2017 |

OTHER PUBLICATIONS

International Search Report and Written Opinion of the International Searching Authority, Application No. PCT/US2017/036968, dated Aug. 23, 2017, 14 pages.

(Continued)

*Primary Examiner* — Sean H Nguyen
(74) *Attorney, Agent, or Firm* — Sunstein LLP

(57) ABSTRACT

A method of signal processing to generate hearing implant stimulation signals for a hearing implant system includes transforming an input sound signal into band pass signals each representing an associated frequency band of audio frequencies. The band pass signals are processed in a sequence of sampling time frames and iterative steps to produce a noise power estimate. This includes using a noise prediction model to determine if a currently observed signal sample includes a target signal, and if so, then updating a current noise power estimate without using the currently observed signal sample, and otherwise updating the current noise power estimate using the currently observed signal sample. The noise prediction model also is adapted based on the updated noise power estimate. The hearing implant (Continued)

stimulation signals are then developed from the band pass signals and the noise power estimate.

18 Claims, 10 Drawing Sheets

(51) Int. Cl.
 *G10L 21/0232* (2013.01)
 *A61N 1/36* (2006.01)
 *A61N 1/05* (2006.01)
(52) U.S. Cl.
 CPC ........ *G10L 21/0232* (2013.01); *A61N 1/0541* (2013.01); *A61N 1/36036* (2017.08); *H04R 25/50* (2013.01); *H04R 2225/43* (2013.01); *H04R 2225/67* (2013.01)
(58) Field of Classification Search
 USPC ......................................................... 381/317
 See application file for complete search history.

(56) References Cited

U.S. PATENT DOCUMENTS

| | | | |
|---|---|---|---|
| 2008/0172108 A1* | 7/2008 | Zierhofer | A61N 1/36036 607/57 |
| 2010/0249880 A1* | 9/2010 | Aschbacher | A61N 1/36036 607/57 |
| 2012/0213395 A1 | 8/2012 | Rosenkranz | |
| 2013/0191118 A1 | 7/2013 | Makino | |
| 2014/0056435 A1 | 2/2014 | Kjems et al. | |
| 2017/0303053 A1* | 10/2017 | Falch | G10L 21/02 |

OTHER PUBLICATIONS

Constantin Wiesener et al., *Adaptive Noise Reduction for Real-time Applications*, AES Convention 128, May 2010, XP040509431, 7 pages.

European Patent Office, Extended European Search Report, Application No. 17813862.4, dated May 23, 2019, 10 pages.

* cited by examiner

RECURSIVE NOISE POWER ESTIMATION WITH NOISE MODEL ADAPTATION

This application claims priority to U.S. Provisional Patent Application 62/349,175, filed Jun. 13, 2016, which is incorporated herein by reference in its entirety.

TECHNICAL FIELD

The present invention relates to hearing implant systems, and more specifically, to techniques for producing electrical stimulation signals in such systems based on estimates and predictions of noise powers in the input sound signals.

BACKGROUND ART

A normal ear transmits sounds as shown in FIG. 1 through the outer ear 101 to the tympanic membrane (eardrum) 102, which vibrates the ossicles of the middle ear 103 (malleus, incus, and stapes). The stapes footplate is positioned in the oval window 106 that forms an interface to the fluid filled inner ear (the cochlea) 104. Movement of the stapes generates a pressure wave in the cochlea 104 that stimulates the sensory cells of the auditory system (hair cells). The cochlea 104 is a long narrow duct wound spirally around its central axis (called the modiolus) for approximately two and a half turns. The cochlea 104 includes an upper channel known as the scala vestibuli, a middle channel known as the scala media and a lower channel known as the scala tympani. The hair cells connect to the spiral ganglion cells of the cochlear nerve 113 that reside in the modiolus. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

FIG. 2 shows various functional blocks in a signal processing arrangement for producing electrode stimulation signals to electrode contacts in an implanted cochlear implant array according to a typical hearing implant system. A pseudo code example of such an arrangement can be set forth as:

Input Signal Preprocessing:
    BandPassFilter (input_sound, band_pass_signals)
Envelope Extraction:
    BandPassEnvelope (band_pass_signals, band_pass_envelopes)
Stimulation Timing Generation:
    TimingGenerate (band_pass_signals, stim_timing)
Pulse Generation:
    PulseGenerate (band_pass_envelopes, stim_timing, out_pulses)

The details of such an arrangement are set forth in the following discussion.

In the signal processing arrangement shown in FIG. 2, the initial input sound signal is produced by one or more sensing microphones, which may be omnidirectional and/or directional. Preprocessor Filter Bank 201 pre-processes this input sound signal with a bank of multiple parallel band pass filters (e.g. Infinite Impulse Response (IIR) or Finite Impulse Response (FIR)), each of which is associated with a specific band of audio frequencies. For example using a filter bank with K digital Butterworth Infinite Impulse Response (IIR) type band pass filters of 6th order, so that the acoustic audio signal is filtered into some K band pass signals $y_1$ to $y_K$ where each signal corresponds to the band of frequencies for one of the band pass filters. Each output of sufficiently narrow band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 201. The Preprocessor Filter Bank 201 also may perform other initial signal processing functions such as and without limitation automatic gain control (AGC) and/or noise reduction and/or wind noise reduction and/or beamforming and other well-known signal enhancement functions. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $y_1$ to $y_K$ (which can also be thought of as electrode channels) are output to a Stimulation Timer 206 that includes an Envelope Detector 202 and Fine Structure Detector 203. The Envelope Detector 202 extracts characteristic envelope signals outputs $Y_1, \ldots, Y_K$ that represent the channel-specific band pass envelopes. The envelope extraction can be represented by $Y_k = LP(|y_k|)$, where |.| denotes the absolute value and LP(.) is a low-pass filter; for example, using 12 rectifiers and 12 digital Butterworth low pass filters of 2nd order, IIR-type. Alternatively, the Envelope Detector 202 may extract the Hilbert envelope, if the band pass signals $U_1, \ldots, U_K$ are generated by orthogonal filters.

The Fine Structure Detector 203 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$. The band pass signals $y_1, \ldots, y_K$ can be assumed to be real valued signals, so in the specific case of an analytic orthogonal filter bank, the Fine Structure Detector 203 considers only the real valued part of $y_K$. The Fine Structure Detector 203 is formed of K independent, equally-structured parallel sub-modules.

The extracted band-pass signal envelopes $Y_1, \ldots, Y_K$ from the Envelope Detector 202, and the stimulation timing signals $X_1, \ldots, X_K$ from the Fine Structure Detector 203 are output from the Stimulation Timer 206 to a Pulse Generator 204 that produces the electrode stimulation signals Z for the electrode contacts in the implanted electrode array 205. The Pulse Generator 204 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 204 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference. The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

In signal processing of electronic communications signals such as for hearing implants, the input sound signal y[n] can be characterized as an additive mixture of an information bearing target signal s[n] and a non-information bearing noise signal d[n]. To extract the information from the target signal s[n], clearly it is desirable to minimize the effects of the noise signal d[n]. Accomplishing such minimization typically requires estimation of the noise power from signal d[n].

R. Martin, *Noise Power Spectral Density Estimation Based on Optimal Smoothing and Minimum Statistics*, IEEE Trans. Speech Audio Proc., Vol. 9, No. 5, July 2001 (incorporated herein by reference in its entirety) describes a classic approach for estimating noise power in an input communications signal without a voice activity detector, tracking the spectral minima of the power spectrum of the noisy signal in frequency bands over a relatively long time window of typically 1-3 seconds. One drawback of this method is the limited tracking performance—if the noise power changes over time, the long observation window prevents the noise power estimate from following the changing noise power with little or no delay. This leads then to an underestimation of the noise power. But making the observation window shorter might lead to overestimation of the noise power since no speech pause might occur within the short window.

R. C. Hendriks, et. al., *Noise tracking using DFT domain subspace decompositions*, IEEE Trans. Audio, Speech, and Lang. Proc., Vol. 16, no. 3, March 2008 (incorporated herein by reference in its entirety) also requires no voice activity detector and achieves a better noise power tracking by an eigenvalue decomposition of correlation matrices constructed from time series of noisy discrete Fourier time (DFT) coefficients. It attains a good tracking performance for changing noise power, but at the cost of a high calculation effort due to the need of the eigenvalue decomposition. A year later, R. C. Hendriks, et. al., *Fast noise PSD-estimation with low complexity*, Proc. of the 34$^{th}$ IEEE Int. Conf. on Acoustics, Speech, and Signal Proc., April 2009 (incorporated herein by reference in its entirety) proposes an algorithm with similar noise power tracking, but with lower computational requirements. This method is based on the construction of high-resolution periodograms per frequency band/DFT bin in a lower resolution filter bank. Although no eigenvalue decomposition is necessary, the computation of a high resolution periodogram is necessary, making this approach also computationally demanding.

R. C. Hendriks, et. al., *MMSE based noise PSD tracking with low complexity*, Proc. of the 35$^{th}$ IEEE Int. Conf. on Acoustics, Speech, and Signal Proc., March 2010 (incorporated herein by reference in its entirety) proposes a Noise Power Spectral Density Estimation based on using Minimum Mean Square Estimators (MMSE), which offers better tracking performance. T. Gerkmann, R. C. Hendriks, *Unbiased MMSE-Based Noise Power Estimation With Low Complexity and Low Tracking Delay*, IEEE Trans. Audio, Speech, and Lang. Proc., Vol. 20, no. 4, May 2012 shows that this MMSE noise estimation can be interpreted as a voice activity detector-based power estimator, which requires prior knowledge of the a priori signal-to-noise ratio (SNR) that is typically not known in advance, though this can be approximated assuming a uniformly distributed SNR over a relatively wide range with a fixed value.

U.S. Pat. No. 8,634,581 (incorporated herein by reference in its entirety) uses a combined approach for estimation of the noise level. The input signal level is compared against a threshold that is derived from the estimated noise level at the previous time frame and a fixed multiplication factor (recursive). Based on this comparison, a first estimate of the noise level for the current time frame is built. A second mechanism derives a second estimate for the noise level at the current time frame by using a codebook. The larger of the two estimates is finally used as the noise level estimate.

U.S. Pat. No. 8,385,572 (incorporated herein by reference in its entirety) describes a noise reduction method that uses a multitude of models for the target signal and/or the interfering noise signal. The motivation for this approach lies in the fact that known noise reduction methods (e.g., Y. Ephraim, D. Malah, Speech Enhancement using a Minimum Mean-Square Error Short-Time Spectral Amplitude Estimator, IEEE Trans. Acoustics, Speech, and Sig. Proc., Vol. ASSP-32, no. 6, December 1984; or R. Martin, *Speech Enhancement based on Minimum Mean-Square Error Estimation and Supergaussian Priors*, IEEE Trans. Speech Audio Proc., vol. 13, no. 5, pp. 845-856, September 2005, both incorporated herein by reference in their entireties) rely on assumptions of the signal statistics (target signal and/or noise signal), assuming typically a Gaussian or supergaussian distribution. These assumptions might not always match reality equally well, which therefore limits the achievable performance of a noise reduction algorithm relying on these signal models. To achieve a better match with reality in terms of signal statistics, and therefore potentially increasing the performance of a noise reduction algorithm, a variety of signal models and a selection procedure for selecting the best match to reality are proposed, using, e.g., a situation classification algorithm. Based on a quality metric provided by the user, the noise and signal models can also be exchanged, e.g., by the hearing aid acoustician and remain static during daily usage. An alternative approach using dynamic models is also described, whereby the models are trained by an algorithm using the input signal and situation detection.

SUMMARY

Embodiments of the present invention are directed to a method of signal processing to generate hearing implant stimulation signals for a hearing implant system. An input sound signal characterized as an additive mixture of an information bearing target signal and a non-information bearing noise signal is transformed into multiple band pass signals each representing an associated frequency band of audio frequencies. The band pass signals are then processed in a sequence of sampling time frames and iterative steps to produce a noise power estimate. For each time frame and iteration the processing includes using a noise prediction model to determine if a currently observed signal sample includes the target signal. If so, then a current noise power estimate is updated without using the currently observed signal sample. Otherwise, the current noise power estimate is updated using the currently observed signal sample. The noise prediction model also is adapted based on the updated noise power estimate. The hearing implant stimulation signals are developed from the band pass signals and the noise power estimate for delivery to an implanted portion of the hearing implant system.

In further specific embodiments, updating the current noise power estimate using the currently observed signal sample may include using the current signal power and the estimated noise power from an immediately preceding time frame and a last iteration step. Updating the current noise power estimate without using the currently observed signal sample may include maintaining constant the current noise power estimate, or additionally using a weighted sum of neighboring noise power estimates with suitably chosen weights and parameters.

Using the noise prediction model to determine if the currently observed signal sample includes the target signal may be based on a hard decision comparison of the currently observed signal sample to a variable threshold; for example, a likelihood ratio test-statistic. Or it may be based on a probability-based decision comparison of the currently observed signal sample to a variable threshold using a speech absence probability function; for example, a sigmoidal function.

The noise prediction model may be a time variant noise model. For example, the noise prediction model may be based on previous time frame noise power estimates and/or previous iteration power estimates. The noise prediction model may be a first order autoregressive model; for example, based on estimates from neighboring sub-bands, or a linear autoregressive model of a linear combination of estimated noise power of a previous iteration and two directly neighboring sub-bands, or a linear autoregressive model of a linear combination of already estimated noise powers and estimated noise power of a preceding iteration and two neighboring noise power estimates, or a nonlinear model where predicted noise power is a nonlinear function with respect to estimated noise powers.

Adapting the noise prediction model may be based on a difference between the noise prediction model and the noise power estimate and/or a continuous adaptation of one or more model optimization criteria such as a mean squared error of a prediction error Adapting the noise prediction model may be performed after all the iterative steps for a given time frame n have been performed, or after each iteration for a given time frame.

Developing the hearing implant stimulation signals may include using the noise power estimate for noise reduction or channel selection of the band pass signals, or for a power saving functionality of the hearing implant system.

DETAILED DESCRIPTION

Embodiments of the present invention are directed to an improved approach to blind estimation of the noise power in an input sound signal y[n] characterized as an additive mixture of an information bearing target signal s[n] (e.g., speech) and a non-information bearing disturbing (noise) signal d[n]:y[n]=s[n]+d[n], where n is the time-index, referred to as the time frame. In particular, the problem of detecting time frames when the target signal s[n] is absent is addressed. In those time-frames, an estimate for the noise power can be updated by using the (observable) input sound signal y[n], since then y[n]=d[n]. The noise power estimate is recursively reused to update the prediction for the next estimation step. This approach differs from existing methods such as described in U.S. Pat. No. 8,385,572 in that no signal model is directly used in a noise power estimation algorithm.

Estimating the noise power can be useful for a number of signal processing applications in a hearing implant system. These applications include:

Noise reduction purposes—Sub-band signals with a poor signal-to-noise ratio (SNR) in a given time frame can be attenuated to improve the SNR, and thus users potentially enjoy better speech perception in noise.

Cochlear implant (CI) signal coding—Selecting only electrode channels with a high SNR or low noise power for stimulation can offer an improved hearing experience.

Power saving strategies—During noise-only situations, the stimulation pattern can be changed to save power, e.g., by reducing the stimulation rate and/or amplitude.

Figure 1:
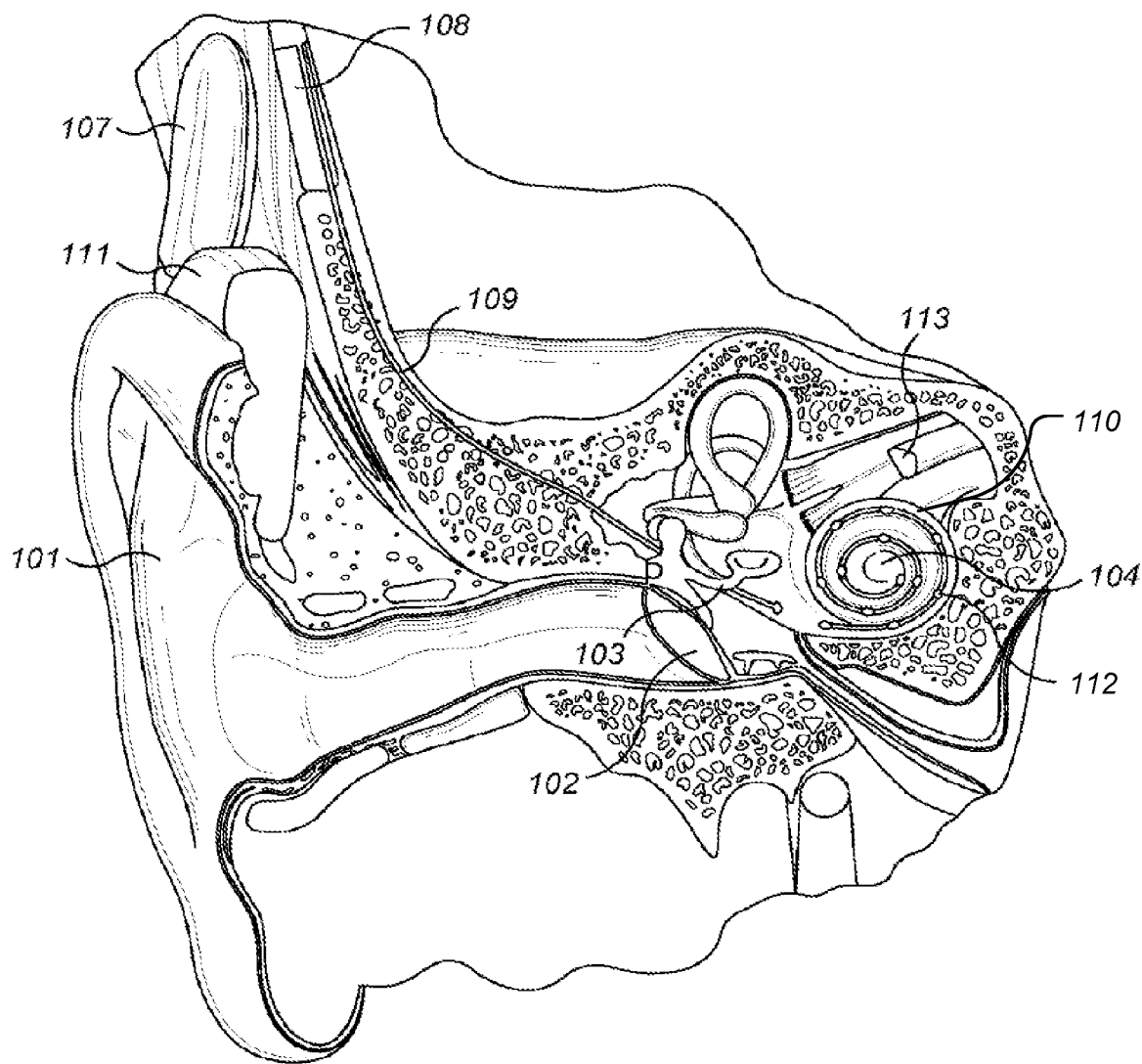
FIG. 1 shows anatomical structures of a typical human ear with a cochlear implant system.
Figure 2:
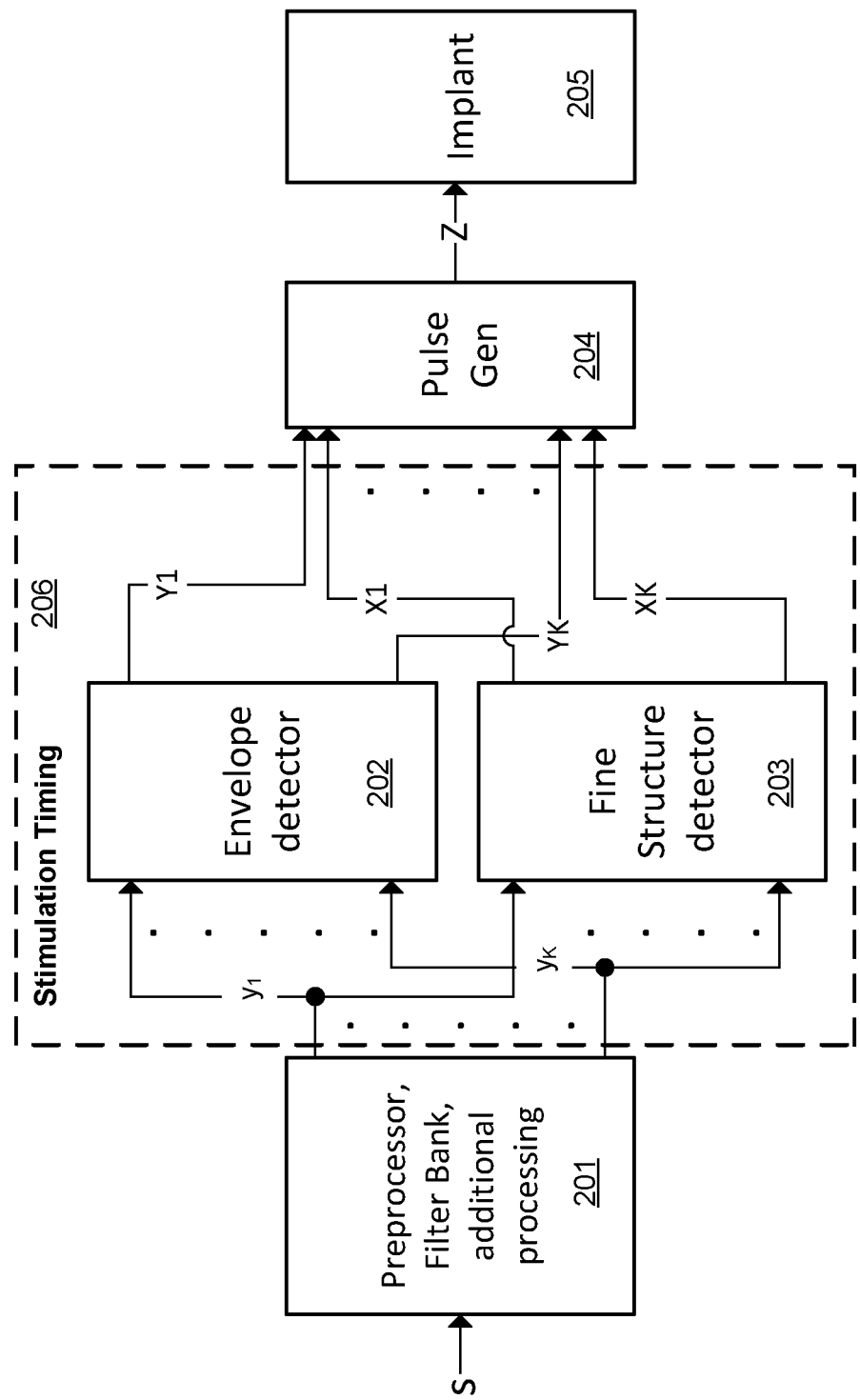
FIG. 2 shows various functional blocks in a signal processing arrangement for a typical cochlear implant system.
Figure 3:
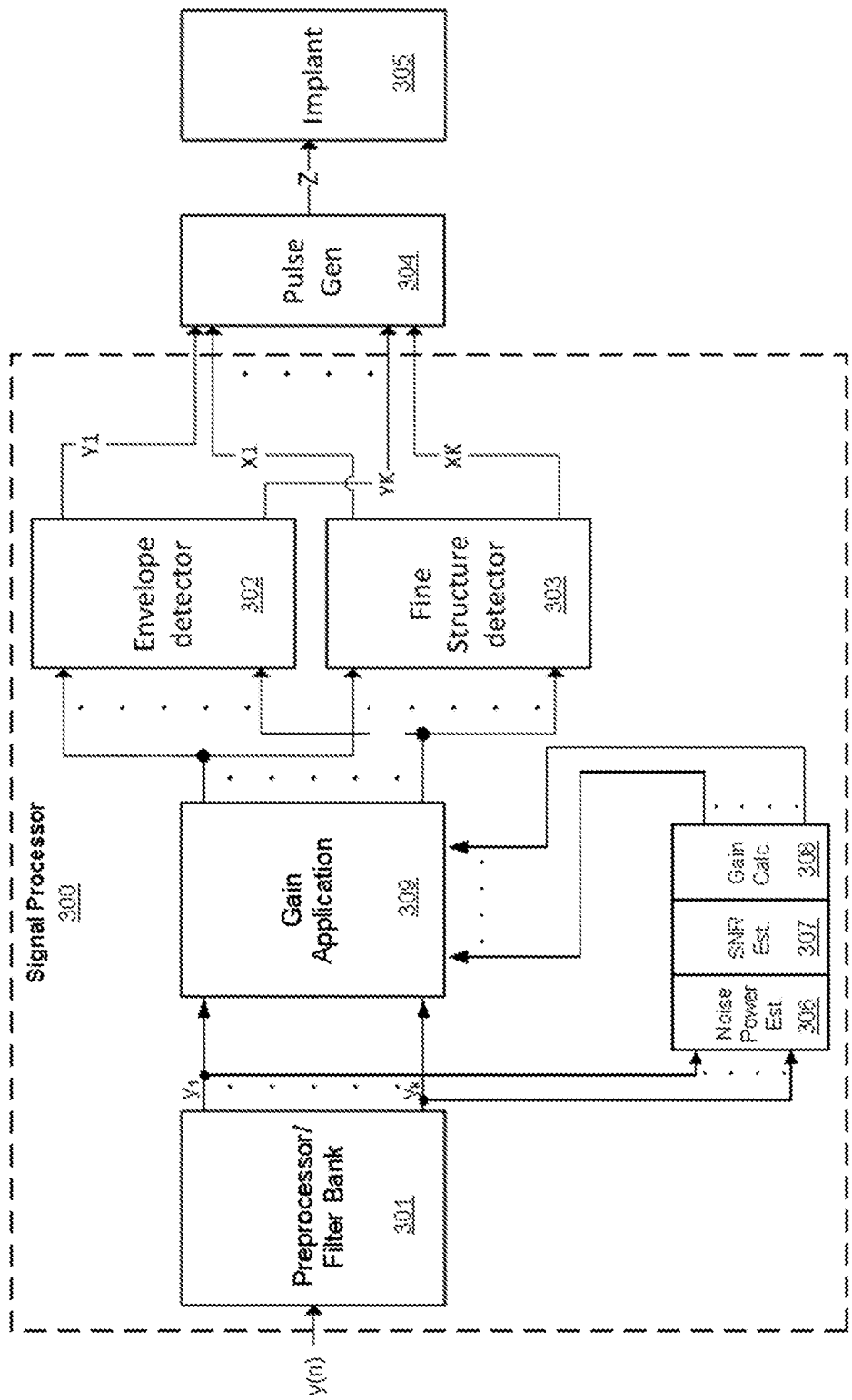
FIG. 3 shows various functional blocks in a signal processing arrangement for a cochlear implant system according to an embodiment of the present invention.
Figure 4:
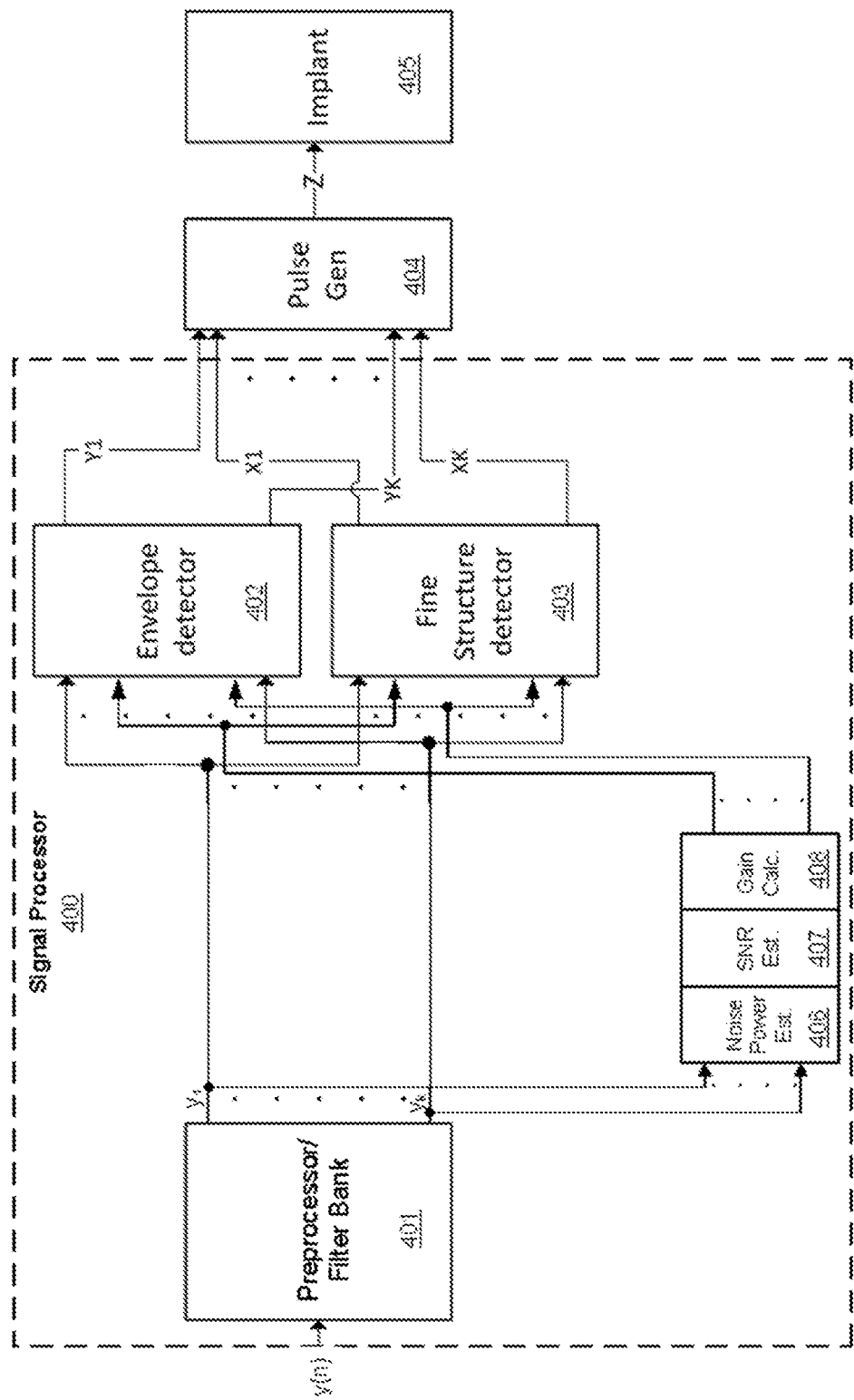
FIG. 4 shows various functional blocks in a signal processing arrangement for a cochlear implant system according to another embodiment of the present invention.

FIG. 3 shows various functional blocks in a signal processing arrangement for a cochlear implant system according to an embodiment of the present invention which is based on a conventional electrical stimulation-based cochlear implant, where a Preprocessor Filter Bank 201 processes the input sound signal y[n] to perform analog-to-digital conversion and apply an analysis filter bank to generate band pass signals $y_k[n]$ each representing an associated frequency band of audio frequencies which also are associated with a set of corresponding auditory neurons. In addition, the Envelope Detector 302, Fine Structure Detector 303, Pulse Generator 304, and Implant 305, operate basically as discussed above with respect to FIG. 2. The arrangement shown in FIG. 3 also has additional processing stages arranged in a noise reduction system for Noise Power Estimation 306, SNR Estimation 307, and Gain Calculation 308 to determine gain factors based on the noise power estimate $\hat{P}_d[n, k, l]$ that is applied on the frequency sub-bands by a Gain Application 309. The hearing implant stimulation signals Z are developed from the band pass envelope signals $Y_k[n]$ and the fine structure signals $X_k[n]$ for delivery to an implanted portion of the hearing implant system. FIG. 4 shows various functional blocks in a signal processing arrangement for a cochlear implant system according to another embodiment of the present invention where noise power and/or SNR estimation is similarly performed and used for sound coding purposes. The Envelope Detector 402, Fine Structure Detector 403, Pulse Generator 404, Noise Power Estimation 406, SNR Estimation 407, Gain Calculation 408 and Implant 405 operate basically as discussed above with respect to FIG. 2 or 3. Different to FIG. 3, where the Gain Application 309 stage precedes Envelope Detector 302 and Fine Structure Detector 303, the output of Gain Calculation 408 is feed for application to the stages Envelope Detector 402 and Fine Structure Detector 403 directly. In this example gain application is integrated into the respective stage and might apply gain factors $\hat{P}_d[n, k, l]$ independently from each other, i.e. Fine Structure Detector 403 may apply the gain factors differently than Envelope Detector 402. In one embodiment Fine Structure Detector 403 and Envelope Detector 402 may apply the gain factors dependent from each other, for example given a certain functional relationship. The functional relationship may for example depend on a cross-correlation property.

In such systems, the Noise Power Estimation Module 306 splits the estimation of the unknown noise power into three main steps:

1. Prediction—First, the noise power is predicted for the current point in time using a model of the underlying noise process. Based on the prediction, a decision is made as to the presence or absence of speech.
2. Estimation—Using the speech presence decision, the current noise power estimate is updated.
3. Adaptation—And the updated noise power estimate is used to update the noise prediction model that predicts the noise power for the next step.

It is assumed that the estimate will be closer to the true value of the noise power than the predicted value is. The increase in information about the unknown noise power after the estimation step is used to improve the noise model. Thus the prediction for the next step is improved, enabling a more accurate decision regarding speech presence or absence.

Prediction and estimation can be performed several times for the same time point n, so that the Noise Power Estimation Module 306 processes the band pass signals $y_k[n]$ in a sequence of sampling time frames n and iterative steps i=1, . . . , I to produce a noise power estimate $\hat{P}_d[n, k, I]$. For each time frame n and iteration i, the Noise Power Estimation Module 306 uses a noise prediction model $\check{P}_d[n, k, i]$ to determine if a currently observed signal sample $P_y[n, k]$ includes the target signal s[n]. If the currently observed signal sample $P_y[n, k]$ includes the target signal s[n], then a current noise power estimate $\hat{P}_d[n, k, i]$ is updated without using the currently observed signal sample $P_y[n, k]$. Otherwise, if the currently observed signal sample $P_y[n, k]$ does not include the target signal s[n], then the current noise power estimate $\hat{P}_d[n, k, i]$ is updated using the currently observed signal sample $P_y[n, k]$. The noise prediction model $\check{P}_d[n, k, i]$ also is adapted based on the updated noise power estimate $\hat{P}_d[n, k, i]$. Performing multiple iterative steps increases the probability of a correct decision regarding speech presence or absence, and thus leads to a more accurate noise power estimate $\hat{P}_d[n, k, I]$.

The observed target signal s[n] and noise signal d[n] are assumed to be realizations of locally stationary stochastic processes in which the statistics of the processes (e.g., represented by statistical moments such as mean and variance) are allowed to change slowly over time. For example, the signal powers are time-variant, but remain more or less constant within a short time window. The time window within which the noise process can be regarded as being stationary (i.e., the moments don't change) is assumed to be longer than that of the target (speech) process. In addition, it is assumed that the noise and speech processes are statistically independent with zero mean. Using the second assumption the signal power is $P_y = E\{(s+d)^2\} = E(s^2) + E(d^2) = P_s + P_d$. That is, simply the addition of the speech power and noise power, where $E\{\cdot\}$ denotes statistical expectation.

Typically, the input sound signal y[n] is decomposed into a number of sub-bands using, e.g., a filter bank (time domain, DFT, other subspaces, . . . ): $y_k[n]=FB(y[n])$, k=1, . . . , K. The processing is typically performed per time and sub-band. If not needed, time and sub-band indices are suppressed in the following. Since the expectation operation cannot be performed in a real implementation, it is typically approximated using an average over time, e.g., by using a low pass filter. The estimated signal power is then $P_y = \langle (s+d)^2 \rangle = \langle s^2 \rangle + \langle d^2 \rangle = P_s + P_d$, where $\langle \cdot \rangle$ denotes averaging over time. Either the squared signal as stated above or, equivalently, the squared envelope is used. For speech processing applications the low pass filter has typically a 6 dB cut-off frequency of approximately 5-50 Hz, which comprises the speech modulations. After low pass filtering, a sampling rate decimation to a significantly lower sampling rate (e.g., 80-100 Hz) can be applied in order to reduce the computational complexity of the following stages.

Figure 5:
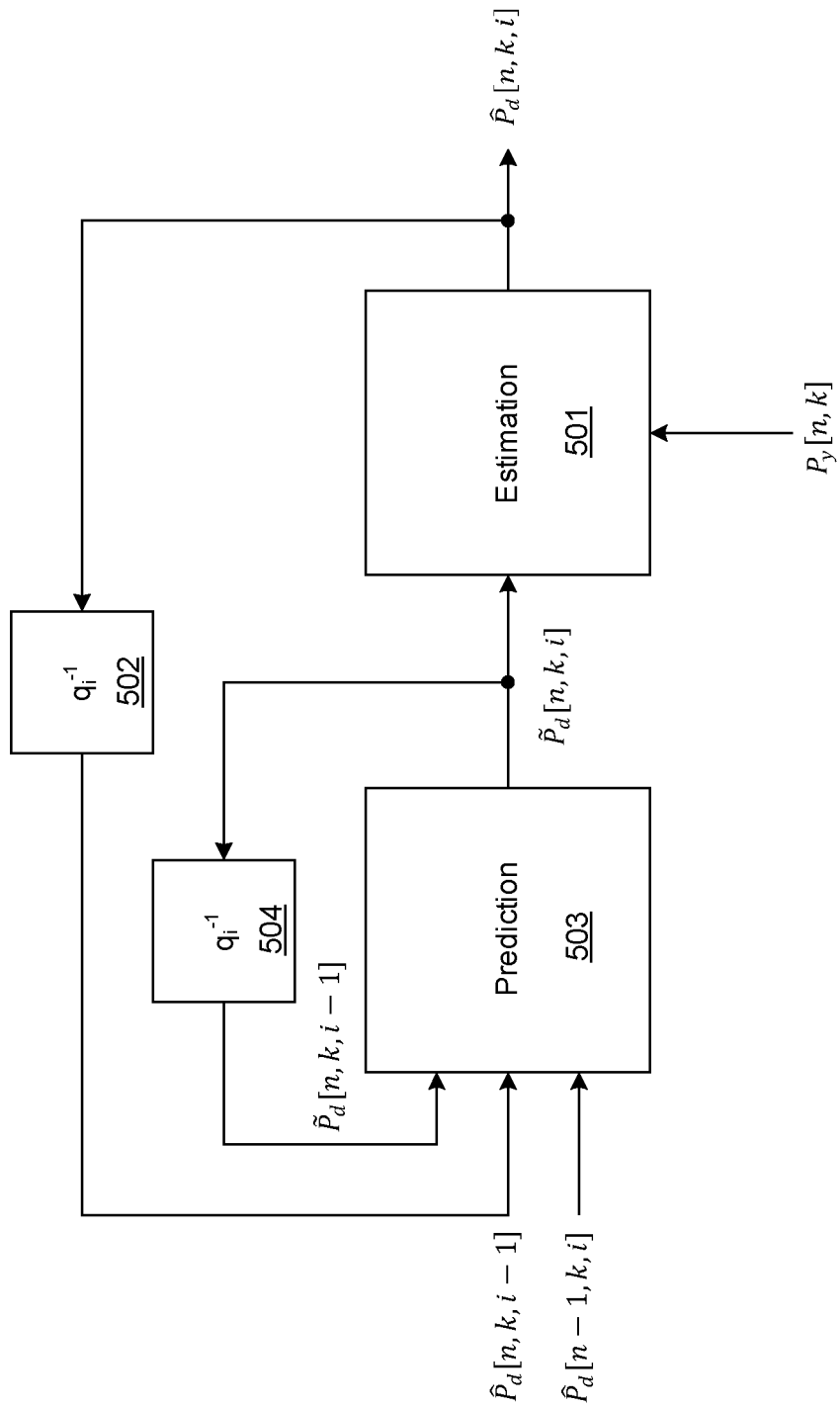
FIG. 5 shows functional blocks in an iterative noise power estimation process with prediction and estimation.

FIG. 5 shows functional blocks in an iterative noise power estimation process with prediction and estimation, where for time frame n, and iterative step i, with iteration memory elements $q_i^{-1}$ 502 and 504 for iteration index i: $q_i^{-1}x[n, i]=x[n, i-1]$. To decide whether the currently observed signal sample $P_y[n, k]$ contains both the target signal s[n] and noise signal d[n], or only the noise signal d[n], Estimation Module 501 performs an iterative hypothesis test. If the Estimation Module 501 decides that the currently observed signal sample $P_y[n, k]$ contains only a noise signal d[n], then the Estimation Module 501 updates the current noise power estimate $\hat{P}_d[n, k, i]$ using the signal sample $P_y[n, k]$. If the Estimation Module 501 decides that the currently observed signal sample $P_y[n, k]$ contains both the target signal s[n] and noise signal d[n], then the Estimation Module 501 updates the current noise power estimate $\hat{P}_d[n, k, i]$ without using the current signal sample $P_y[n, k]$, either keeping the current noise power estimate $\hat{P}_d[n, k, i]$ constant, or updating it using a number of neighbouring noise power estimates for other sub-bands other than bank k.

More specifically, the hypothesis test at iteration i is a simple comparison of the current sample $P_y$ against a variable threshold $\eta$:

$P_y[n, k] \leq \eta[n, k, i]$: $P_y[n, k]$ consists of noise only (null-hypothesis $H_0$)

$P_y[n, k] > \eta[n, k, i]$: consists of noise and speech (hypothesis $H_1$).

The noise power estimate $\hat{P}_d[n, k, i]$ is then constructed based on the hypothesis-test decision. Recursive smoothing over time n and/or sub-band k may also be applied by which the correlation of the noise power over time and/or sub-bands is taken into account. If the hypothesis test indicates that the speech signal s[n] is absent (null-hypothesis $H_0$), then the noise power estimate $\hat{P}_d[n, k, i]$ is updated using the current signal sample $P_y[n, k]$ and the estimated noise power from time point n−1 and the last iteration step I, $\hat{P}_d[n-1, k, I]$:

$$\hat{P}_{d,sa}[n,k,i] = \alpha \hat{P}_d[n-1,k,I] + (1-\alpha)P_y[n,k]$$

Using a hard threshold decision, the noise power estimate is then:

$$P_y[n,k] \leq \eta[n,k,i] : \hat{P}_d[n,k,i] = \hat{P}_{d,sa}[n,k,i].$$

If the null-hypothesis is rejected (speech is present), the noise power estimate $\hat{P}_d[n, k, i]$ is kept constant, i.e., $$\hat{P}_{d,sp}[n,k,i] = \hat{P}_d[n-1,k,I].$$

The update of the noise power estimate is then $$P_y[n,k] > \eta[n,k,i] : \hat{P}_d[n,k,i] = \hat{P}_{d,sp}[n,k,i].$$

Alternatively, in the case of speech present, the noise power estimate $\hat{P}_d[n, k, i]$ can be updated using additionally a weighted sum of neighbouring noise power estimates, $$\hat{P}_{d,sp}[n, k, i] = (1-\gamma)\hat{P}_d[n-1, k, I] + \gamma \tilde{P}_d[n-1, k, I]$$

with $$\tilde{P}_d[n-1, k, I] = \sum_{l \neq k}^{K} w_{l,k} \hat{P}_d[n-1, l, I]$$

with suitably chosen weights $w_{l,k}$, e.g., $$w_{l,k} = \alpha \exp(-b|l-k|^m)$$

and suitably chosen parameters a, b, m. With this weighting, distant sub-bands contribute less than neighbouring sub-bands, reflecting, e.g., a decrease of the correlation if the distance in frequency increases. The weights $w_{l,k}$ and/or the parameters a, b, m can also be estimated and updated continuously using already existing noise power estimates from time frames before n or from time frame n and previous iterations i. The smoothing parameters α (in case speech absent) and γ (speech present) determine the degree of influence of the noise power estimate from time frame n−1 and model in a simple manner the correlation of the noise power over time.

Instead of a hard threshold decision as described above, a soft threshold decision could be used and might be advantageous since errors regarding the decision of speech absence or presence would have less weight. The output of the comparison with the threshold η is defined as speech absence probability. A decision $$p[n,k,i]=g(\eta[n,k,i],P_y[n,k]),$$

with a suitable function g (•) providing (soft) values for the speech-absent probability in the interval [0,1] can be used. E.g., a sigmoidal function $$p[n,k,i] = \frac{1}{1+e^{-\beta_k t[n,k,i]}},$$

with $$t[n,k,i] = \eta[n,k,i] - P_y[n,k]$$

and $\beta_k$ determining the steepness of the function. A hard decision is achieved for the limit case $\beta_k \to \infty$. Using the speech absence probability p[n, k, i], the noise power estimate at iteration i, time frame n, and sub-band k is then $$\hat{P}_d[n,k,i]=p[n,k,i]\hat{P}_{d,sa}[n,k,i]+(1-p[n,k,i])\hat{P}_{d,sp}[n,k,i],$$

with the speech-presence probability 1−p[n, k, i]. For the first simple case described above, the noise power estimate is then $$\hat{P}_d[n,k,i] = p[n,k,i]\hat{P}_{d,sa}[n,k,i] + (1-p[n,k,i])\hat{P}_{d,sp}[n,k,i] =$$
$$= p[n,k,i](\alpha\hat{P}_d[n-1,k,I] + (1-\alpha)P_y[n,k]) +$$
$$(1-p[n,k,i])\hat{P}_d[n-1,k,I]$$
$$= (1-\tilde{p}[n,k,i])\hat{P}_d[n-1,k,I] + \tilde{p}[n,k,i]P_y[n,k]$$

with a scaled speech-absence probability $\tilde{p}[n, k, i]$=p[n, k, i](1−α).

The threshold can be derived using a stochastic signal model that treats the involved signals $P_y$, $P_s$, $P_d$ as stochastic processes, using a likelihood ratio test-statistic (Neyman, J., Pearson, E., *On the problem of the most efficient test of statistical hypotheses*, Philosophical Transactions of the Royal Society of London, Series A, Containing Papers of a Mathematical or Physical Character 231, pp. 289-337, 1933; incorporated herein by reference in its entirety):

$$\Lambda(P_y) = \frac{L(P_y | H_1)}{L(P_y | H_0)} = \frac{f_{P_y}(P_y | P_s \neq 0)}{f_{P_y}(P_y | P_s = 0)}$$

where $f_{P_y}(P_y|P_s)$ is the conditional probability density function (amplitude distribution) of the process $P_y$ given $P_s$. The likelihood-ratio is compared to a threshold $\Lambda(P_y)>\eta$, and decided in favour of hypothesis $H_1$ (speech present) if the inequality holds. The aim is to maximise the probability of a correct decision (to detect speech present if speech is in fact present) for a given probability of false-alarm $p_{FA}$ (deciding for speech present when speech is in fact absent). The false-alarm probability is the probability that the test-statistic $\Lambda(P_y)$ is larger than the threshold if in fact speech is absent, i.e., hypothesis $H_0$ is in force $$p_{FA}=p[\Lambda(P_y)>\eta|H_0]=\int_{\{P_y:\Lambda(P_y)>\eta\}}f_{P_y}(P_y|P_s)dP_y.$$

With this equation, the threshold for a given false-alarm probability can be determined.

The threshold is a function of the unknown noise power $P_d$ since $P_y=P_s+P_d$. In order to be able to calculate a threshold, a prediction $\tilde{P}_d[n]$ of the unknown noise power for time n as discussed below is used. This yields for the threshold $\eta[n]=\eta(p_{FA}, \tilde{P}_d[n])$ where the function $\eta(\cdot)$ depends on the assumed probability density $f_{P_y}(P_y|P_s)$.

The key for an accurate estimation of the noise power is a correct decision whether the currently observed sample $P_y[n]$ results from speech and noise or noise only. This decision is based on the threshold calculation and depends on the targeted false-alarm probability and the noise-power. Since the noise-power is unknown and the aim of the process, the threshold cannot be calculated directly. Instead, a predicted value for the unknown noise power based on a time-variant noise-model can be used based on previous noise power estimates $\hat{P}_d[n-1, k, I]\hat{P}_d[n-2, k, I], \ldots$ as well as estimates produced at previous iteration steps, i.e., $\hat{P}_d[n, k, i-1], \hat{P}_d[n, k, i-2], \ldots$. A prediction for the noise power for the current iteration step then can be made by using, e.g., an auto regressive model of first order (AR-1):

$$\tilde{P}_d[n,k,i]=f(\theta,\hat{P}_d[n-1,k,I],\hat{P}_d[n,k,i-1]),$$

where $\theta=[\theta_1, \theta_2, \ldots, \theta_M]^T$ are the model parameters. In some specific embodiments, estimates from neighbouring sub-bands can be used in the prediction model, too:

$$\tilde{P}_d[n,k,i]=f(\theta,\hat{P}_d[n-1,k,I],\hat{P}_d[n,k,i-1],\hat{P}_d[n-1,l\neq k,I],\hat{P}_d[n,l\neq k,i-1]).$$

The prediction model parameters θ for the noise power are adapted to increase the accuracy of succeeding predictions. This is done by using the final estimate for the noise power at time n and iteration-end I, $\hat{P}_d[n, k, I]$ and the prediction $\tilde{P}[n, k, I]$. Specifically, the difference between the two gives information about the mismatch between the model and the actual noise process, and is used for adapting the model parameters. Since the model is adapted, the parameters are changing over time, i.e., the (linear or non-linear) model itself changes over time. The adaptation rule as described further below defines how the parameters are adapted to the current situation.

For predicting the noise-power, various different specific models can be used; for example, a linear AR-11 model in which the predicted noise power is a linear combination of the estimated noise power of the previous iteration and two directly neighbouring sub-bands:

$$\tilde{P}_d[n,k,i] = \sum_{l=max(k-1,1)}^{min(k+1,K)} \theta_l[n,k]\hat{P}_d[n,l,i-1]$$

whereby for i=1, $\hat{P}_d[n, k, 0]=\hat{P}_d[n-1, k, I]$, i.e., the estimate from the previous time frame n−1. Or a linear AR-ML model could be employed where the predicted noise power is a linear combination of M already estimated noise powers and the estimated noise power of the last iteration, as well as 2 L neighbouring noise power estimates:

$$\tilde{P}_d[n,k,i] =$$
$$\sum_{l=max(k-1,k)}^{min(k+1,K)} \theta_{0l}[n,k]\hat{P}_d[n,l,i-1] + \sum_{m=1}^{M}\sum_{l=min(k+L,K)}^{max(k-L,1)} \theta_{ml}[n,k]\hat{P}_d[n-m,l,I].$$

Or a nonlinear model could be used where the predicted noise power is a nonlinear function with respect to the estimated noise powers, in which case, many different alternatives can be implemented, such as a recursive polynomial model.

For a linear-in-the-parameters prediction model, the model parameters can be condensed into a vector and the prediction is written as $\tilde{P}_d[n, k, i] = \psi_{n,k,i}^T \theta_{n,k}$. For a linear AR-11 model:

$$\psi_{n,k,i}^T = [\hat{P}_d[n,k-1,i-1], \hat{P}_d[n,k,i-1], \hat{P}_d[n,k+1,i-1]]$$

and:

$$\theta_{n,k}^T = [\theta_{-1}[n,k], \theta_0[n,k], \theta_{+1}[n,k]].$$

Figure 6:
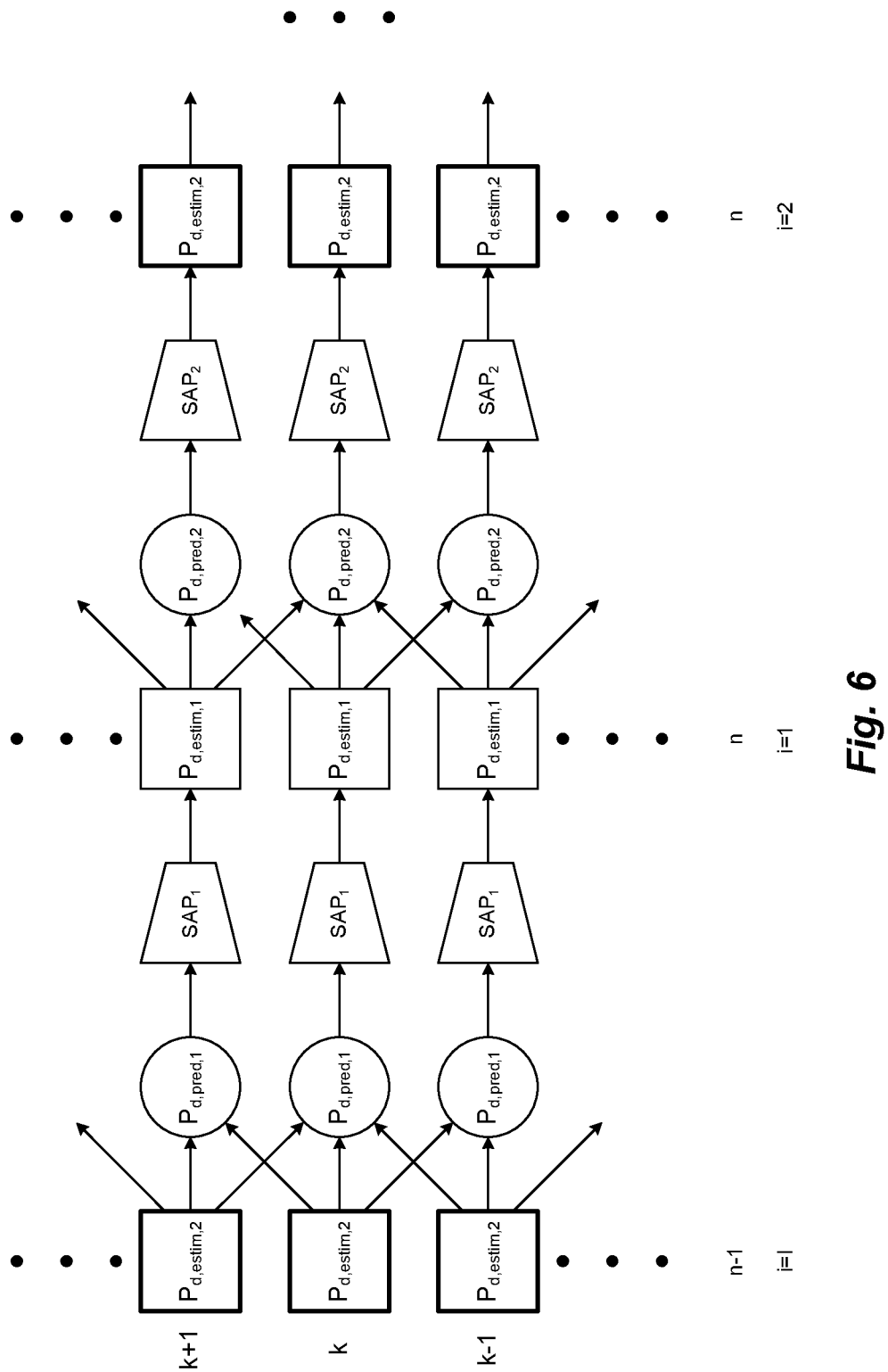
FIG. 6 shows an example of iterative noise power estimation with two prediction steps and two estimation steps.

FIG. 6 shows an example for I=2 iteration steps where the estimate of time frame n−1 is available. The first step in the first iteration is to predict the noise power for time n. In the example, the prediction is based on the estimated noise power at n−1, k, k−1, k+1. Based on the predicted noise power, the speech-absence probability (sap, p[n, k, i=1]) is calculated. Using the speech-absence probability, the noise power for time frame n and iteration i=1 is calculated. These calculations are performed for all sub-bands, before the next iteration is initiated. By performing more than one iteration per time frame opens the possibility to correct suboptimal estimations, e.g., due to a wrong decision regarding speech presence.

Two cases, reflecting two situations prone for a false decision for speech presence or absence can be briefly considered. In a case where there is a rising noise power and speech is absent, then it is likely that it might be decided for speech presence due to the increasing signal power. If at time frame n, sub-band k, iteration i=1 it was erroneously decided for speech presence, the noise power estimate is not updated and will not follow the increasing noise power, i.e., it will be too small. If in the neighbouring sub-bands k−1, k+1 the decision is correct, the estimates for the noise power are updated correctly and increase. In the next iteration step, the prediction for the noise power in sub-band k is based on the updated noise power estimates in the neighbouring sub-bands and will increase also, assuming the noise model is sufficiently accurate. The probability for a correct speech presence or absence decision at this iteration step is increased now since the noise power prediction will be more accurate, and thus the decision for speech absence more likely, resulting in a larger probability for an update of the noise power estimate.

In a different case where there is a falling noise power and speech is present, it is likely that it might be decided for speech absent due to the decreasing signal level. That is, it might happen that at time frame n, sub-band k, iteration i=1, it is decided for speech absent. The noise power then will be updated erroneously. Assuming correct decisions and updates in the neighbouring sub-bands, i.e., decreasing noise power estimates there, at iteration i=2 it might be decided for speech presence, leading to a correct update of the noise power.

Figure 7A:
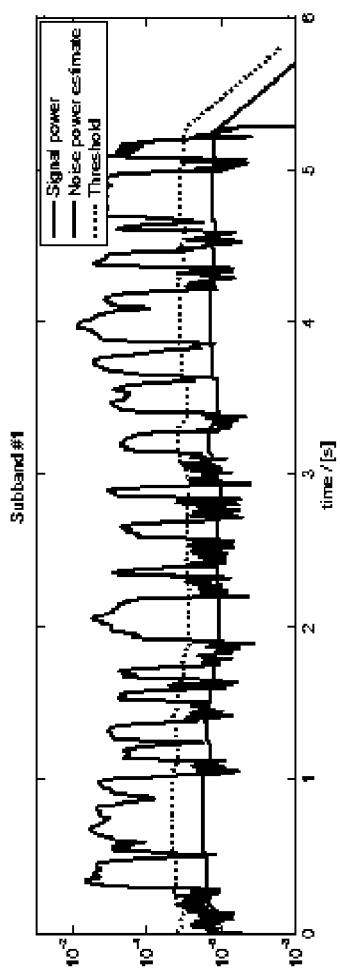
FIGS. 7A and 7B show a speech waveform in white noise with signal power, estimated noise power and threshold traces.
Figure 7B:
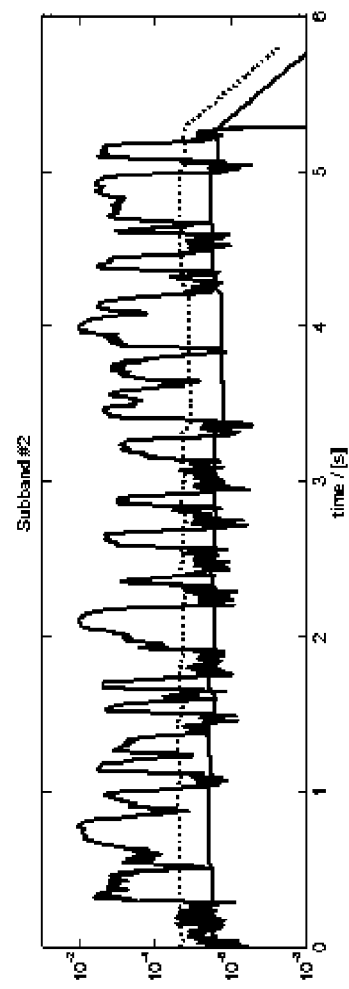

With this method, the speech absence probability is iteratively calculated, and, due to the correlation across sub-bands, it is assumed that a false decision at one iteration step is corrected in one of the following steps. FIGS. 7A and 7B show a simple estimation example with speech in white noise. Two sub-bands are shown along with the estimated noise power and the threshold. The threshold in this example is derived from a time-invariant prediction model considering only one estimated noise power sample from the same sub-band.

Figure 8:
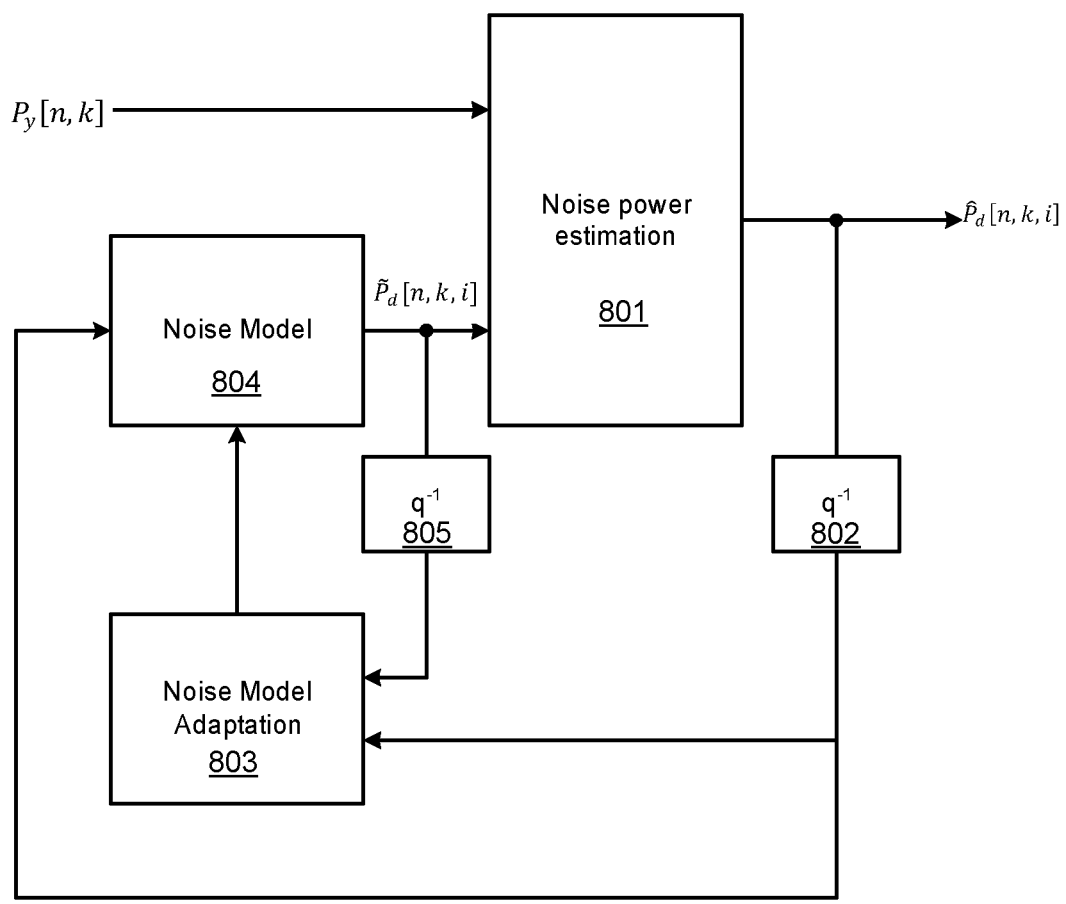
FIG. 8 shows functional blocks in an iterative noise power estimation process with prediction, estimation and adaptation.

FIG. 8 shows functional blocks in an iterative noise power estimation process with a Noise Power Estimation Module 801, Noise Prediction Model 804, Noise Model Adaptation Module 803, and iteration memory elements $q_i^{-1}$ 802 and 805 for iteration index i. Within the Adaptation Module 803 the prediction model parameters are adapted using the information gained in the estimation step. Specifically, the difference is used between the prediction and the estimation in the last iteration step $\tilde{P}_d$(n, k, I) and $\hat{P}_d$(n, k, I). It is assumed that in the estimation step the knowledge about the unknown noise power increases, as compared with the prediction. The prediction is just used for deciding for speech presence or not. Even if the prediction is not very accurate, the decision regarding speech presence might be correct. If the decision regarding speech presence is correct, in the estimation step the knowledge about the unknown noise power is increased and this gain in information is exploited for adapting the prediction model. The model-parameters are continuously adapted according to an optimisation criterion such as to minimise the mean squared error of the prediction error $J = E\{e[n, k, I]^2\}$, with the prediction error:

$$e[n,k,I] = \hat{P}_d[n,k,I] - \tilde{P}_d[n,k,I].$$

The prediction model parameters can then be adapted, e.g., using a steepest decent method $$\theta_{n,k} = \theta_{n-1,k} - \mu \nabla_\theta J$$

with a fixed (or time variant) step-size μ determining the adaptation accuracy and tracking speed. Typically, since the expectation E{•} cannot be calculated due to lack of knowledge of the statistics of the prediction error, a stochastic gradient decent method can be used, e.g., the least mean square (LMS) method $$\theta_{n,k} = \theta_{n-1,k} - \mu \nabla_\theta e[n,k,I]^2 = \theta_{n-1,k} + \mu \psi_{n,k,I} e[n,k].$$

Advantageously, the adaptation considers only cases where the probability for a good noise power estimation is high, i.e., cases when it is relatively sure that speech is not present, since then the noise power was estimated accurately with high probability. For a AR-11 prediction model with $$\psi_{n,k,I}^T = [\hat{P}_d[n,k-1,I], \hat{P}_d[n,k,I], \hat{P}_d[n,k+1,I]]$$

the fixed step-size turns into a 3×3 diagonal time-variant step-size matrix, $$Q_{n,k,I} = \mu \begin{pmatrix} p[n, k-1, I] & 0 & 0 \\ 0 & p[n, k, I] & 0 \\ 0 & 0 & p[n, k+1, I] \end{pmatrix},$$

incorporating the speech-absent probabilities. With this matrix step-size, the update equation reads $$\theta_{n,k} = \theta_{n-1,k} + Q_{n,k,I} \psi_{n,k,I} e[n,k],$$

thus restricting model adaptation more or less to speech-absent periods.

Figure 9:
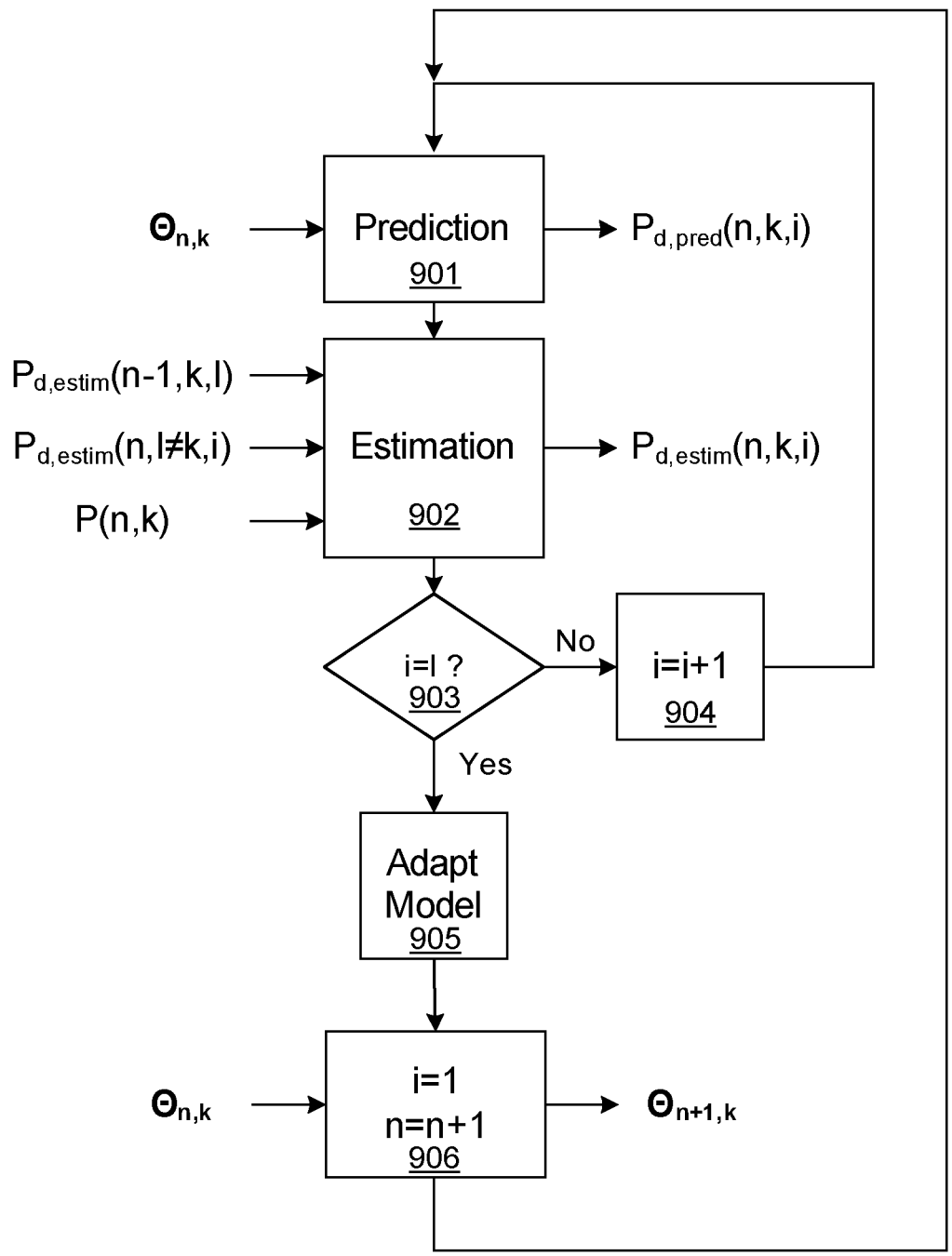
FIG. 9 shows a flow chart algorithm of prediction, estimation and adaptation where the adaptation is outside the iteration loop.

Adaptation and iteration are interleaved with at least two possible methods. FIG. 9 shows a flow chart algorithm of prediction, step 901, estimation in step 902 and adaptation in step 905 where the adaptation is outside the iteration loop so that the model is adapted after all iteration steps I have been performed. Thus during the iterations within loop formed by steps 903 and 904, the model parameters are kept constant and the estimated noise power in the model $\hat{P}_d[n, k, i−1]$ is updated from i−1 to i. Finally at step 906 the time-instant is incremented and the algorithm for the next time-instant restarted.

Figure 10:
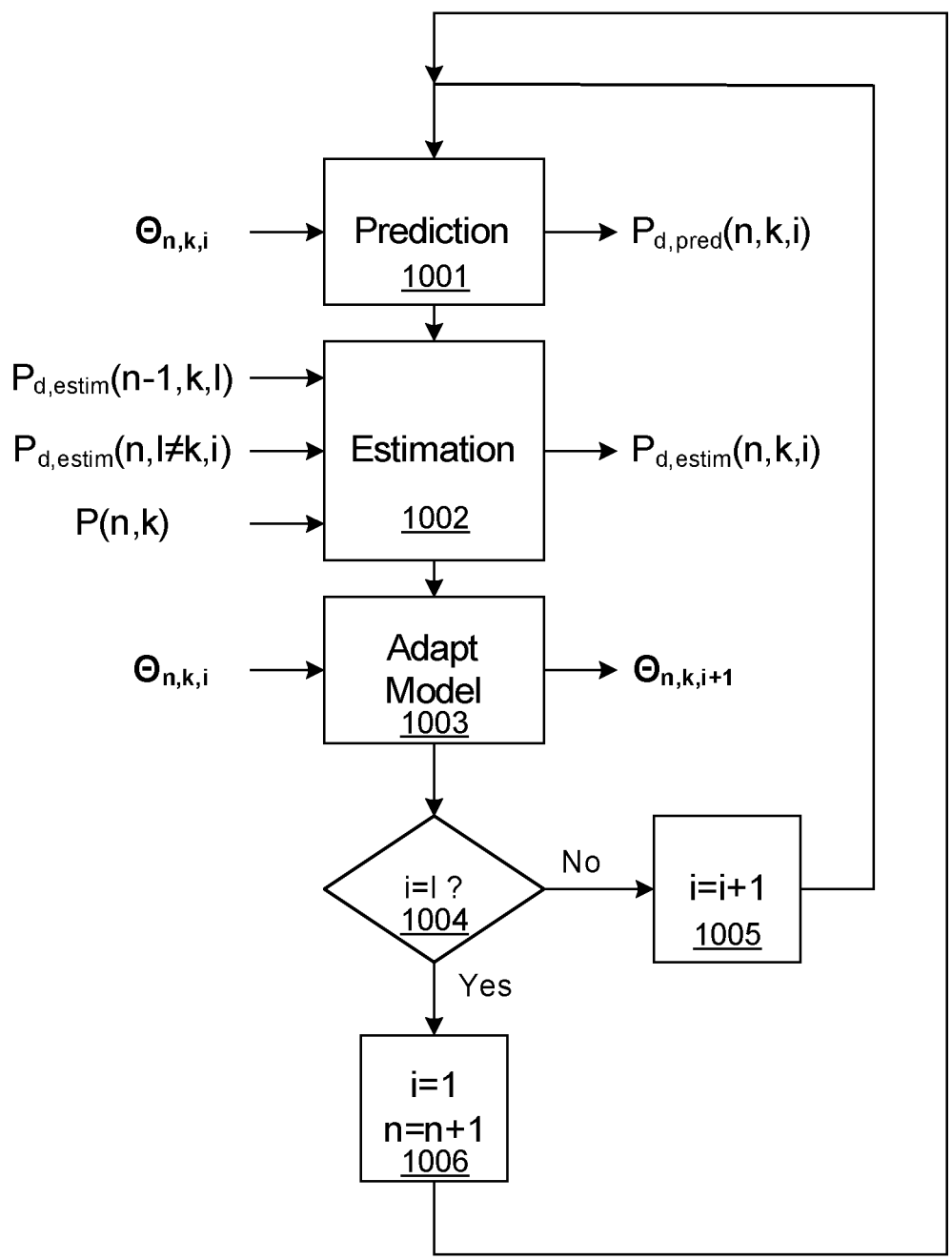
FIG. 10 shows a flow chart algorithm of prediction, estimation and adaptation where the adaptation is inside the iteration loop.

FIG. 10 shows a flow chart algorithm of prediction, step 1001, estimation in step 1002 and adaptation in step 1003 where the adaptation is inside the iteration loop formed by steps 1004 and 1005 so that the model is adapted at each iteration step. Thus, after iteration i, the model parameters are updated prior to the next iteration step at advancing to the next time-instant in step 1006. In this case, the prediction error is calculated based on the prediction and estimation of the noise power at the current iteration.

Due to the recursive approach described above, changing noise power over time can be tracked with only a short delay. And due to the adaptation of the prediction model, the system is able to adapt to various acoustical situations, especially adaptation to various noise types. In addition, this approach is of relatively low arithmetical complexity compared to existing arrangements. Of course, due to the recursive approach, a system might become unstable for some unfavourable combination of parameters and input signal.

Embodiments of the invention may be implemented in part by any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of signal processing to generate hearing implant stimulation signals Z for a hearing implant system, the method comprising:
   transforming an input sound signal y[n] characterized as an additive mixture of an information bearing target signal s[n] and a non-information bearing noise signal d[n] into a plurality of band pass signals $y_k[n]$ each representing an associated frequency band of audio frequencies;
   processing the band pass signals $y_k[n]$ in a sequence of sampling time frames n and iterative steps i=1, . . . , I to produce a noise power estimate $\hat{P}_d[n,k,I]$, wherein for each time frame n and iteration i, the processing includes:
   i. using a noise prediction model $\tilde{P}_d[n,k,i]$ to determine if a currently observed signal sample $P_y[n,k]$ includes the target signal s[n], wherein using the noise prediction model is based on a hard decision comparison of the currently observed signal sample to a variable threshold, the variable threshold representing a likelihood ratio test-statistic $$\Lambda(P_y) = \frac{L(P_y \mid H_1)}{L(P_y \mid H_0)} = \frac{f_{P_y}(P_y \mid P_s \neq 0)}{f_{P_y}(P_y \mid P_s = 0)}.$$

ii. if the currently observed signal sample $P_y[n,k]$ includes the target signal s[n], then updating a current noise power estimate $\tilde{P}_d[n,k,i]$ without using the currently observed signal sample $P_y[n,k]$, and otherwise
   iii. if the currently observed signal sample $P_y[n,k]$ does not include the target signal s[n], then updating a current noise power estimate $\hat{P}_d[n,k,i]$ using the currently observed signal sample $P_y[n,k]$,
      wherein processing the band pass signals $y_k[n]$ further comprises adapting the noise prediction model $\tilde{P}[n,k,i]$ based on the updated noise power estimate $\hat{P}_d[n,k,i]$; and
   developing the hearing implant stimulation signals Z from the band pass signals $y_k[n]$ and the noise power estimate $\hat{P}_d[n,k,I]$.

2. The method according to claim 1, wherein updating the current noise power estimate $\hat{P}_d[n,k,i]$ using the currently observed signal sample $P_y[n,k]$ includes using the current signal power $P_y[n,k]$ and the estimated noise power from an immediately preceding time frame n−1 and a last iteration step I, $\hat{P}_d[n−1,k,I]$ so that the current noise power estimate $\hat{P}_d[n,k,i]=\alpha\hat{P}_d[n−1,k,I]+(1−\alpha)P_y[n,k]$, where α is a smoothing parameter.

3. The method according to claim 1, wherein updating the current noise power estimate $\hat{P}_d[n,k,i]$ without using the currently observed signal sample $P_y[n,k]$ includes maintaining constant the current noise power estimate $\hat{P}_d[n,k,i]$.

4. The method according to claim 1, wherein updating the current noise power estimate $\hat{P}_d[n,k,i]$ without using the currently observed signal sample $P_y[n,k]$ includes additionally using a weighted sum of neighboring noise power estimates, $\hat{P}_d[n,k,i]=(1−\gamma)\hat{P}_d[n−1,k,I]+\gamma\tilde{P}_d[n−1,k,I]$ with $\tilde{P}_d[n−1,k,I]=\Sigma_{l\neq k}^{K} w_{l,k}\hat{P}_d[n−1,l,I]$ with suitably chosen weights $w_{l,k}$ and parameters a, b, m, γ.

5. The method according to claim 1, wherein adapting the noise prediction model $\tilde{P}_d[n,k,i]$ is performed after all I iterative steps for a given time frame n have been performed.

6. The method according to claim 1, wherein adapting the noise prediction model $\tilde{P}_d[n,k,i]$ is performed after each iteration i for a given time frame n.

7. The method according to claim 1, wherein developing the hearing implant stimulation signals includes using the noise power estimate $\tilde{P}_d[n,k,I]$ for noise reduction of the band pass signals $y_k[n]$.

8. The method according to claim 1, wherein developing the hearing implant stimulation signals includes using the noise power estimate $\tilde{P}_d[n,k,I]$ for channel selection of the band pass signals $y_k[n]$.

9. The method according to claim 1, wherein developing the hearing implant stimulation signals includes using the noise power estimate $\tilde{P}_d[n,k,I]$ for a power saving functionality of the hearing implant system.

10. The method according to claim 1, wherein developing the hearing implant stimulation signals includes using the noise power estimate $\hat{P}_d[n,k,I]$ for channel selection of the band pass signals $y_k[n]$.

11. A method of signal processing to generate hearing implant stimulation signals Z for a hearing implant system, the method comprising:

transforming an input sound signal y[n] characterized as an additive mixture of an information bearing target signal s[n] and a non-information bearing noise signal d[n] into a plurality of band pass signals $y_k[n]$ each representing an associated frequency band of audio frequencies;

processing the band pass signals $y_k[n]$ in a sequence of sampling time frames n and iterative steps i=1, ..., I to produce a noise power estimate $\hat{P}_d[n,k,I]$, wherein for each time frame n and iteration i, the processing includes:

i. using a noise prediction model $\tilde{P}_d[n,k,i]$ to determine if a currently observed signal sample $P_y[n,k]$ includes the target signal s[n], wherein using the noise prediction model is based on a probability-based decision comparison of the currently observed signal sample $P_y[n,k]$ to a variable threshold $\eta[n,k,i]$, using a speech absence probability p[n,k,i] in an interval [0,1], where p[n,k,i]=g($\eta[n,k,i],P_y[n,k]$), so that the noise power estimate $\hat{P}_d[n, k, i]$ at iteration i, time frame n, and sub-band k is $\hat{P}_d[n,k,i]$=p[n,k,i] $\hat{P}_{d,sa}[n,k,i]$+(1-p[n,k,i])$\hat{P}_{d,sp}[n,k,i]$, ii. if the currently observed signal sample $P_y[n,k]$ includes the target signal s[n], then updating a current noise power estimate $\tilde{P}_d[n,k,i]$ without using the currently observed signal sample $P_y[n,k]$, and otherwise iii. if the currently observed signal sample $P_y[n,k]$ does not include the target signal s[n], then updating a current noise power estimate $\tilde{P}[n,k,i]$ using the currently observed signal sample $P_y[n,k]$, wherein processing the band pass signals $y_k[n]$ further comprises adapting the noise prediction model $\tilde{P}_d[n,k,i]$ based on the updated noise power estimate $\hat{P}_d[n,k,i]$; and developing the hearing implant stimulation signals Z from the band pass signals $y_k[n]$ and the noise power estimate $\hat{P}_d[n,k,I]$.

12. The method according to claim 11, wherein the speech absence probability p[n,k,i] is a sigmoidal function where $$p[n, k, i] = \frac{1}{1 + e^{-\beta_k t[n,k,i]}},$$

with a steepness determined by t[n,k,i]=$\eta$[n,k,i]-$P_y$[n,k] and $\beta_k$.

13. A method of signal processing to generate hearing implant stimulation signals Z for a hearing implant system, the method comprising:

transforming an input sound signal y[n] characterized as an additive mixture of an information bearing target signal s[n] and a non-information bearing noise signal d[n] into a plurality of band pass signals $y_k[n]$ each representing an associated frequency band of audio frequencies;

processing the band pass signals $y_k[n]$ in a sequence of sampling time frames n and iterative steps i=1, ..., I to produce a noise power estimate $\hat{P}_d[n,k,I]$, wherein for each time frame n and iteration i, the processing includes:

i. using a noise prediction model $\tilde{P}_d[n,k,i]$ to determine if a currently observed signal sample $P_y[n,k]$ includes the target signal s[n], wherein using the noise prediction model $\tilde{P}_d[n,k,i]$ is a time variant noise model that is a first order autoregressive model $\tilde{P}[n,k,i]$=f($\theta,\hat{P}_d[n-1,k,I]\hat{P}_d[n,k,i-1]$) with model parameters $\theta=[\theta_1, \theta_2, \ldots, \theta_M]^T$, ii. if the currently observed signal sample $P_y[n,k]$ includes the target signal s[n], then updating a current noise power estimate $\tilde{P}_d[n,k,i]$ without using the currently observed signal sample $P_y[n,k]$, and otherwise iii. if the currently observed signal sample $P_y[n,k]$ does not include the target signal s[n], then updating a current noise power estimate $\tilde{P}[n,k,i]$ using the currently observed signal sample $P_y[n,k]$, wherein processing the band pass signals $y_k[n]$ further comprises adapting the noise prediction model $\tilde{P}_d[n,k,i]$ based on the updated noise power estimate $\hat{P}_d[n,k,i]$; and developing the hearing implant stimulation signals Z from the band pass signals $y_k[n]$ and the noise power estimate $\hat{P}_d[n,k,I]$.

14. The method according to claim 13, wherein the noise prediction model $\tilde{P}_d[n,k,i]$ is based on estimates from neighboring sub-bands $\tilde{P}_d[n,k,i]$=f($\theta,\hat{P}_d[n-1,k,I],\hat{P}_d[n,k,i-1],\hat{P}_d[n-1,l\neq k,I],\hat{P}_d[n,l\neq k,i-1]$).

15. A method of signal processing to generate hearing implant stimulation signals Z for a hearing implant system, the method comprising:

transforming an input sound signal y[n] characterized as an additive mixture of an information bearing target signal s[n] and a non-information bearing noise signal d[n] into a plurality of band pass signals $y_k[n]$ each representing an associated frequency band of audio frequencies;

processing the band pass signals $y_k[n]$ in a sequence of sampling time frames n and iterative steps i=1, ..., I to produce a noise power estimate $\hat{P}_d[n,k,I]$, wherein for each time frame n and iteration i, the processing includes:

i. using a noise prediction model $\tilde{P}_d[n,k,i]$ to determine if a currently observed signal sample $P_y[n,k]$ includes the target signal s[n], wherein the noise prediction model $\tilde{P}_d[n,k,i]$ is a time variant noise model that is a linear autoregressive model of a linear combination of estimated noise power of a previous iteration and two directly neighboring sub-bands, $\tilde{P}_d[n,k,i]=\Sigma_{i=k-1}^{k+1}\theta_l[n,k]\hat{P}_d[n,l,i-1]$, where for i=1, $\hat{P}_d[n,k,0]=\hat{P}_d[n-1,k,I]$, representing estimated noise power from previous time frame n−1, ii. if the currently observed signal sample $P_y[n,k]$ includes the target signal s[n], then updating a current noise power estimate $\hat{P}_d[n,k,i]$ without using the currently observed signal sample $P_y[n,k]$, and otherwise iii. if the currently observed signal sample $P_y[n,k]$ does not include the target signal s[n], then updating a current noise power estimate $\hat{P}_d[n,k,i]$ using the currently observed signal sample $P_y[n,k]$, wherein processing the band pass signals $y_k[n]$ further comprises adapting the noise prediction model $\tilde{P}[n,k,i]$ based on the updated noise power estimate $\hat{P}_d[n,k,i]$; and developing the hearing implant stimulation signals Z from the band pass signals $y_k[n]$ and the noise power estimate $\hat{P}_d[n,k,I]$.

16. A method of signal processing to generate hearing implant stimulation signals Z for a hearing implant system, the method comprising:

transforming an input sound signal y[n] characterized as an additive mixture of an information bearing target signal s[n] and a non-information bearing noise signal d[n] into a plurality of band pass signals $y_k[n]$ each representing an associated frequency band of audio frequencies;

processing the band pass signals $y_k[n]$ in a sequence of sampling time frames n and iterative steps i=1, ..., I to produce a noise power estimate $\hat{P}_d[n,k,I]$, wherein for each time frame n and iteration i, the processing includes:

i. using a noise prediction model $\tilde{P}_d[n,k,i]$ to determine if a currently observed signal sample $P_y[n,k]$ includes the target signal s[n], wherein the noise prediction model $\tilde{P}_d[n,k,i]$ is a time variant noise model that is a linear autoregressive model of a linear combination of M already estimated noise powers and estimated noise power of a preceding iteration i−1 and two L neighboring noise power estimates, $\tilde{P}_d[n,k,i]=\Sigma l=k-1^{k+1}\theta_{0l}[n,k]\tilde{P}_d[n,l,i-1]+\Sigma_{m=1}^{M}\Sigma_{i=k-L}^{k+L}\theta_{ml}[n,k]\hat{P}_d[n-m,l,I]$, where for i=1, $\hat{P}_d[n,k,0]=0$, ii. if the currently observed signal sample $P_y[n,k]$ includes the target signal s[n], then updating a current noise power estimate $\hat{P}_d[n,k,i]$ without using the currently observed signal sample $P_y[n,k]$, and otherwise iii. if the currently observed signal sample $P_y[n,k]$ does not include the target signal s[n], then updating a current noise power estimate $\hat{P}_d[n,k,i]$ using the currently observed signal sample $P_y[n,k]$, wherein processing the band pass signals $y_k[n]$ further comprises adapting the noise prediction model $\tilde{P}[n,k,i]$ based on the updated noise power estimate $\hat{P}_d[n,k,i]$; and developing the hearing implant stimulation signals Z from the band pass signals $y_k[n]$ and the noise power estimate $\hat{P}_d[n,k,I]$.

17. A method of signal processing to generate hearing implant stimulation signals Z for a hearing implant system, the method comprising:

transforming an input sound signal y[n] characterized as an additive mixture of an information bearing target signal s[n] and a non-information bearing noise signal d[n] into a plurality of band pass signals $y_k[n]$ each representing an associated frequency band of audio frequencies;

processing the band pass signals $y_k[n]$ in a sequence of sampling time frames n and iterative steps i=1, ..., I to produce a noise power estimate $\hat{P}_d[n,k,I]$, wherein for each time frame n and iteration i, the processing includes:

i. using a noise prediction model $\tilde{P}_d[n,k,i]$ to determine if a currently observed signal sample $P_y[n,k]$ includes the target signal s[n], ii. if the currently observed signal sample $P_y[n,k]$ includes the target signal s[n], then updating a current noise power estimate $\hat{P}_d[n,k,l]$ without using the currently observed signal sample $P_y[n,k]$, and otherwise iii. if the currently observed signal sample $P_y[n,k]$ does not include the target signal s[n], then updating a current noise power estimate $\hat{P}[n,k,i]$ using the currently observed signal sample $P_y[n,k]$, wherein processing the band pass signals $y_k[n]$ further comprises adapting the noise prediction model $\tilde{P}_d[n,k,i]$ based on the updated noise power estimate $\hat{P}_d[n,k,i]$ wherein adapting the noise prediction model $\tilde{P}_d[n,k,i]$ is based on a continuous adaptation of one or more model optimization criteria the one or more model optimization criteria including minimizing a mean squared error $J=E\{e[n,k,I]^2\}$ of a prediction error $e[n,k,I]=\hat{P}_d[n,k,I]-\tilde{P}_d[n,k,I]$; and developing the hearing implant stimulation signals Z from the band pass signals $y_k[n]$ and the noise power estimate $P_d[n,k,I]$.

18. The method according to claim 17, wherein adapting the noise prediction model $\tilde{P}_d[n,k,i]$ is based on adapting parameters of the noise prediction model $\tilde{P}_d[n,k,i]$ using a steepest descent method $\theta_{n,k}=\theta_{n-1,k}-\mu\nabla_\theta J$ with a fixed step size μ.

* * * * *

UNITED STATES PATENT AND TRADEMARK OFFICE
CERTIFICATE OF CORRECTION

PATENT NO. : 10,785,581 B2  
APPLICATION NO. : 16/302711  
DATED : September 22, 2020  
INVENTOR(S) : Aschbacher et al.

Page 1 of 1

It is certified that error appears in the above-identified patent and that said Letters Patent is hereby corrected as shown below:

On the Title Page

Item [72], replace "FLorian" with --Florian--

In the Claims

Column 16, Line 44, Claim 1 replace "$\tilde{P}[n,k,i]$" with --$\tilde{P}_d[n, k, i]$--

Column 17, Line 49, Claim 11 replace "$\hat{P}d,sa[n,k,i]$" with --$\hat{P}_{d,sa}[n, k, i]$--

Column 18, Line 27, Claim 13 replace "$\tilde{P}[n,k,i]$" with --$\tilde{P}_d[n, k, i]$--

Column 18, Line 36, Claim 13 replace "$\hat{P}[n,k,i]$" with --$\tilde{P}_d[n, k, i]$--

Column 19, Line 18, Claim 15 replace "$\tilde{P}[n,k,i]$" with --$\tilde{P}_d[n, k, i]$--

Column 20, Line 28, Claim 17 replace "$\hat{P}_d[n,k,l]$" with --$\tilde{P}_d[n, k, i]$--

Column 20, Line 33, Claim 17 replace "$\hat{P}[n,k,i]$" with --$\tilde{P}_d[n, k, i]$--

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*